United States Patent [19]

Topfl et al.

[11] 4,079,042

[45] Mar. 14, 1978

[54] COPOLYMERS CONTAINING CARBOXY AND ESTER GROUPS, PROCESS FOR THEIR MANUFACTURE AND THEIR USE

[75] Inventors: Rosemarie Topfl, Dornach; Christina Gothberg, Basel, both of Switzerland

[73] Assignee: Ciba-Geigy Corporation, Ardsley, N.Y.

[21] Appl. No.: 721,908

[22] Filed: Sep. 9, 1976

Related U.S. Application Data

[63] Continuation of Ser. No. 590,545, June 26, 1975, abandoned.

[30] Foreign Application Priority Data

Dec. 19, 1974 Switzerland ................... 16979/74

[51] Int. Cl.² ............... C08F 216/18; C08F 216/20; C08F 222/06; C08F 224/00
[52] U.S. Cl. ................................ 260/63 R; 8/115.5; 260/29.6 H; 260/29.6 TA; 424/71; 428/474; 428/483; 428/510; 428/522; 427/385 R; 427/389; 427/390 B
[58] Field of Search ............. 260/63 R; 427/385, 389, 427/390; 428/474, 483, 510, 522

[56] References Cited

U.S. PATENT DOCUMENTS

| | | | |
|---|---|---|---|
| 2,585,537 | 2/1952 | Coffman | 260/78.5 |
| 3,721,654 | 3/1973 | Schlumbom et al. | 260/78.5 |
| 3,776,850 | 12/1973 | Pearson et al. | 252/89 |

FOREIGN PATENT DOCUMENTS

7,311,839  9/1973  Netherlands.

*Primary Examiner*—Stanford M. Levin
*Attorney, Agent, or Firm*—Edward McC. Roberts; Prabodh I. Almaula

[57] ABSTRACT

New copolymers containing carboxy and ester groups, of maleic anhydride, diketene and optionally vinyl alkyl ethers, the alcohol components of the ester groups of said copolymers being derived from ethylene glycol- or polyethylene glycol monoalkyl ethers, alcohols of 1 to 18 carbon atoms or mixtures thereof, and the ratio of carboxy groups to ester groups being 5:1 to 1:5 are provided.

The new copolymers are employed as textile assistants, such as antistatic agents or fabric softeners; they can also be used as non-woven binders, as paper sizing agents or as hair laquers.

16 Claims, No Drawings

COPOLYMERS CONTAINING CARBOXY AND ESTER GROUPS, PROCESS FOR THEIR MANUFACTURE AND THEIR USE

This is a continuation of application Ser. No. 590,545, filed on June 26, 1975, now abandoned.

The present invention provides new copolymers containing carboxy and ester groups, of maleic anhydride, diketene and optionally vinyl alkyl ethers, the alcohol components of the ester groups of said copolymers being derived from ethylene glycol- or polyethylene glycol monoalkyl ethers, alcohols of 1 to 18 carbon atoms or mixtures thereof, and the ratio of carboxy groups to ester groups being 5:1 to 1:5, especially 4:1 to 1:4 or 2:1 to 1:2. The given ratios are substantially in the range of 5:1 to 1:2.

The carboxy group can optionally also be in salt form, e.g. as the alkali metal, alkaline earth metal, ammonium or amine salt.

The copolymers contain recurring units of the formulae

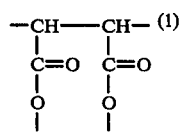  (1)  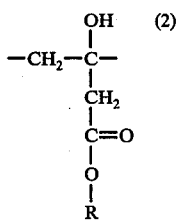  (2)

and optionally

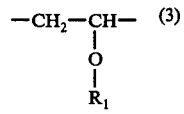  (3)

wherein R is the radical of the alcohol component which is derived from ethylene glycol- or polyethylene glycol monoalkyl ethers, alcohols of 1 to 18 carbon atoms or mixtures thereof, or is hydrogen, $R_1$ is alkyl of 1 to 22, especially 2 to 18 and preferably 2 to 8, carbon atoms and is optionally substituted.

The copolymers normally contain on average 3 to 900, especially 3 to 600 and preferably 6 to 150, units of the formulae (1), (2) and optionally (3) in each molecule. The ratio of units of the formulae (1) : (2) and optionally to (3) is preferably 1 : (0.7 to 0.9) : (0.3 to 0.1). The ratio is usually 1:1 when using copolymers which contain the recurring units of the formulae (1) and (2).

The copolymers according to the invention have as a rule an average molecular weight of 800 to 45,000 and preferably from 1000 to 20,000.

Preferred copolymers contain for example the recurring unit of the formula

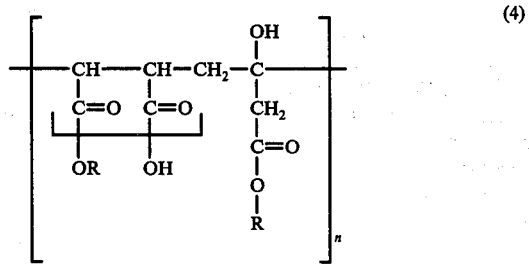  (4)

wherein R has the indicated meaning and n is an integer from 3 to 900, especially 3 to 600 and preferably 6 to 150.

The alcohol component R is as a rule a monohydroxy compound. It is derived e.g. from ethylene glycol monoalkyl ethers of the formula $$R_2OCH_2CH_2OH \quad (5)$$

wherein $R_2$ is alkyl of 1 to 6, preferably 1 to 2, carbon atoms. Examples of such alkyl radicals are: methyl, ethyl, n-propyl, isopropyl, n-butyl, isobutyl, amyl or hexyl.

If derivatives of polyethylene glycol monoalkyl ethers are used as alcohol component, these have the formula $$R_2O(CH_2CH_2O)_nH \quad (6)$$

wherein $R_2$ has the given meaning and is also preferably alkyl of 1 or 2 carbon atoms, i.e. methyl or ethyl, and n is an integer from 2 to 80, preferably 2 to 50.

The alcohol component is further derived from monoalcohols of 1 to 18 carbon atoms and in the event of alcohol mixtures being used, it is desirable to use at least one alcohol of 1 to 8 carbon atoms and one of 9 to 18 carbon atoms.

Examples of suitable alcohol radicals are methyl, ethyl, n-propyl, isopropyl, n-butyl, isobutyl, n-hexyl, 2-ethylhexyl, octyl, nonyl, decyl, dodecyl, palmityl and stearyl. The radicals of 1 to 4 and of 12 to 18 carbon atoms are preferred.

In respect of the acid component, the copolymers according to the invention which contain carboxy and ester groups are copolymers of maleic anhydride, diketene and optionally vinyl alkyl ethers which contain recurring units of the formulae (7) 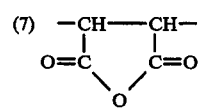  (8) 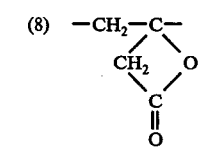

and optionally (9) 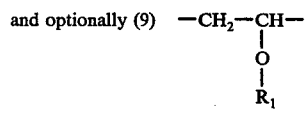

wherein $R_1$ has the given meaning. The radical of the formula (7) is derived from maleic anhydride, that of the formula (8) from diketene and that of the formula (9) from a vinyl alkyl ether. The alkyl radical $R_1$ in the formula (9) contains 1 to 22, preferably 2 to 18 or especially 2 to 8, carbon atoms, can be both branched or unbranched and is substituted or unsubstituted. Examples of such radicals are: methyl, ethyl, n-propyl, isopropyl, n-butyl, isobutyl, n-hexyl, 2-ethylhexyl, n-dodecyl, stearyl or behenyl. The n-butyl radical has proved particularly advantageous.

The maleic anhydride, diketene and the vinyl alkyl ethers used as starting materials for the copolymerisation can be readily obtained and are in part industrial products.

Suitable vinyl ethers contain 1 to 22, preferably 2 to 18 or especially 2 to 8, carbon atoms in the alkyl moiety, which is unsubstituted or substituted e.g. by halogen, especially chlorine or bromine. Examples of such ethers are: vinyl methyl ether, vinyl ethyl ether, vinyl chloroethyl ether, vinyl-n- propyl ether, vinyl isopropyl ether, vinyl-n-butyl ether, vinyl isobutyl ether, vinyl-n-hexyl ether, vinyl-2-ethylhexyl ether, vinyl-n-dodecyl ether, vinyl stearyl ether or vinyl behenyl ether.

The copolymers which contain the recurring units of the formulae (7), (8) and (9) and which are used as starting materials are manufactured by polymerising maleic anhydride, diketene and a vinyl alkyl ether the alkyl moiety of which contains 1 to 22 carbon atoms, in an organic solvent which is inert to the reactants, in the presence of radical initiators or under the influence of electromagnetic waves at temperatures of $-20°$ to $-100°$ C.

The polymerisation is therefore carried out under radical conditions, suitable radical initiators being e.g. $\alpha,\alpha'$-azobisisobutyronitrile or peroxides, or under the influence of electromagnetic waves, i.e. irradiation, for example with ultraviolet light. When using radical initiators, the reaction temperatures are preferably in the range of 40° to 80°; and in the case of irradiation, the preferred temperature range is $-20°$ to $+80°$ C. It is also preferred to carry out the copolymerisation excluding oxygen, especially in vacuo or in a nitrogen atmosphere.

Substantially any solvent which is inert to maleic anhydride, diketene and the vinyl alkyl ether can be used for the process according to the invention. Examples of such solvents are halogenated lower hydrocarbons of 1 to 4, preferably 1 to 2, carbon atoms, cyclic low molecular ethers, and low molecular ketones, benzene and substituted benzenes.

Specific examples of particularly suitable solvents are: acetone, dioxan, tetrahydrofuran, benzene, methylene chloride, chloroform, 1,2-dichloroethane, perchloroethylene and mixtures thereof.

The rate of polymerisation differs according to the solvent used.

Preferably the copolymers according to the invention contain different ester groupings, i.e. mixtures of the indicated hydroxylated compounds are used in the esterification. Such mixtures are: ethylene- or polyethylene glycol monoalkyl ethers and alcohols of 1 to 18, in particular 1 to 8 and preferably 1 to 4, carbon atoms; e.g. methoxypolyethylene glycol and butanol; ethylene- or polyethylene glycol monoalkyl ethers and alcohols of 9 to 18, preferably 12 to 18, carbon atoms, e.g. methoxypolyethylene glycol and stearyl alcohol; ethylene- or polyethylene glycol monoalkyl ethers, alcohols of 1 to 8 and alcohols of 9 to 18 carbon atoms, e.g. methoxypolyethylene glycol, lauryl alcohol or stearyl alcohol and butanol; or alcohols of 1 to 8 carbon atoms and alcohols of 9 to 18 carbon atoms, e.g. butanol and stearyl alcohol.

The copolymers according to the invention which contain carboxy and ester groups are obtained by reacting the copolymers which contain the recurring units of the formulae (7), (8) and optionally (9), with the cited ethylene- or polyethylene glycol monoalkyl ethers and the alcohols of 1 to 18 carbon atoms.

The process for the manufacture of the copolymers which contain carboxy and ester groups comprises reacting a copolymer of maleic anhydride, diketene and optionally vinyl alkyl ethers with an ethylene- or polyethylene glycol monoalkyl ether, an alcohol of 1 to 18 carbon atoms or mixtures thereof, in solvents which are inert to the reactants, optionally in the presence of an acid catalyst, at 80° to 120° C. The esterification is effected by using the cited ethylene- or polyethylene glycol monoethyl ethers or the other alcohols in such an amount that in the recurring units of the polymers according to the invention the ratio of carboxy to ester groups is 5:1 to 1:5, in particular 4:1 to 1:4 or 2:1 to 1:2. The indicated ratios are substantially in the range of 5:1 to 1:2. The amount of the alcohol if esterification component is therefore preferably at most twice the equivalent amount, referred to maleic anhydride, and is preferably 0.5 to 1 equivalent. The reaction can be carried out in ketones, e.g. methyl isobutyl ketone, or in cyclic ethers, e.g. dioxan.

The reaction is optionally carried out in the presence of an acid catalyst. Suitable catalysts can be low molecular organic carboxylic and sulphonic acids, for example formic or acetic acid, benzensulphonic acid or especially p-toluenesulphonic acid.

As a rule, the reaction temperature is in the region of 80° to 120° C, preferably of 90° to 110° C.

The copolymers according to the invention can be used for example as textile assistants, such as antistatic agents or fabric softeners, as binders, e.g. for bonding nonwovens, as paper sizing agents or as hair lacquers in hair cosmetics.

It is preferred to use the copolymers in the form of alkali metal, ammonium or amine salts.

Suitable textile materials which can be treated with the copolymers according to the invention are organic natural and especially synthetic fibrous materials.

As natural fibrous material there may be cited: wool, silk, cotton and jute, and as synthetic material e.g. regenerated cellulose, acetate rayon, polyamide, polyester, polyacrylonitrile, polyolefins or blended fabrics, for example polyamide/polyester or cellulose/polyamide. These materials can by undyed or preferably dyed materials. The materials are preferably in the form of textile fabrics, flocks, yarn or piece goods. As piece goods there may mentioned in particular floor coverings, e.g. carpets, or other home textiles such as upholstery fabrics, curtains or wall coverings.

The fibrous material is finished preferably by spraying, impregnating, slop padding or by the exhaustion process, and optionally also by brushing the copolymers onto it. For this purpose it is possible to use aqueous solutions or dispersions of the copolymers according to the invention which have a solids content of about 10 to 30%, preferably 15 to 30% and a pH of 2.5 to 10, in particular 3 to 8 and preferably 6 to 8.

The component mixture according to the invention is advantageously sprayed uniformly as aqueous dispersion (spray liquor) using spraying equipment onto the wet or dry material to be treated in such an amount that, after the material has been dried at about 80° to 180° C, sufficient component mixture remains on the surface of the material so as to obtain the desired permanent effects.

The treated textile materials, e.g. carpets, exhibit good antistatic effect i.e. no troublesome discharges arise on coming into contact with or treading on them. In addition, the handle, and in the case of dyed materials also the fastness to rubbing and light, is not adversely affected by the finish.

A combined antistatic and dirt repellent finish can be obtained for example with a combination of the copolymers according to the invention and aqueous preparations of N,N-disubstituted acid amides of dicarboxylic and tricarboxylic acids. These acids amides are obtained e.g. from higher molecular weight dialkylamines or from polyalkylene polyamines which are partially acylated by higher molecular weight fatty acids, for example from diethylene triamine which has been acylated with stearic acid, and phthalic acid or trimellitic anhydride or from aliphatic dicarboxylic acids, such as malonic, succinic, adipic and sebacid acid. The application of the combination is effected by known methods and in this connection it is advantageous to use surface active assistants, e.g. alkylphenol/ethylene oxide adducts, to manufacture the aqueous application liquors.

The following Examples will serve to illustrate the invention in more detail, but without restricting it what is described therein.

EXAMPLE 1

98 g (1 mole) of maleic anhydride are dissolved in 150 g of 1,2-dichloroethane. Then 84 g (1 mole) of diketene are added and the solution is heated to an internal temperature of 75° C. The polymerisation is subsequently initiated by addition of 0.5 g of $\alpha,\alpha'$-azobisisobutyronitrile. The previously clear solution becomes immediately turbid and the polymer begins to precipitate. At two-hourly intervals, 0.5 g of $\alpha,\alpha'$-azobisisobutyronitrile is added 7 times. Total duration of the polymerisation: 18 hours. The polymer is filtered off, washed with 1,2-dichloroethane and dried.

Yield: 87.4% of theory.

Molecular weight (vapour pressure osmosis): 1400

The infrared spectrum shows the characteristic bands for anhydride and lactone ring.

The maleic anhydride/diketene/vinyl ether copolymers are manufactured by an analogous process.

EXAMPLE 2

A mixture of 18.2 g (0.1 mole of maleic anhydride equivalent) of maleic anhydride/diketene copolymer (1:1), 19 g (0.07 mole) of stearyl alcohol, 22.5 g (0.03 mole) of methoxypolyethylene glycol 750, 5.9 g (0.08 mole) of n-butanol and 0.2 g of p-toluenesulphonic acid is refluxed for 24 hours in 400 g of dioxan. The dioxan is then removed by vacuum distillation. Yield: 67 g (65 g of dry substance of a wax-like product. Acid number: 135. Viscosity number ($\eta$): 0.086 intrinsic viscosity, measured in this and each of the subsequent Examples at 25° C in acetone). The sodium salt is manufactured by adding 20.8 g of 30% sodium hydroxide solution and 345 g of deionised water and heating the mixture with stirring to about 80° C until the resin is dissolved.

A turbid solution is obtained which can be readily diluted with water.

Solids content: 15%, pH: 7.3.

EXAMPLE 3

A mixture of 18.2 g (0.1 mole of maleic anhydride equivalent) of maleic anhydride/diketene copolymer (1:1), 6.75 g (0.025 mole) of stearyl alcohol, 37.5 g (0.05 mole) of methoxypolyethylene glycol 750, 1.85 g (0.025 mole) of n-butanol and 0.2 g of p-toluenesulphonic acid is refluxed for 24 hours in 360 g of dioxan. The dioxan is then removed by vacuum distillation.

Yield: 69 g (64 g of dry substance) of a wax-like product.

Acid number: 173; viscosity number ($\eta$): 0.084.

The sodium salt is manufactured by adding 26.5 g of 30% sodium hydroxide solution and 224.5 g of deionised water thereto and heating the mixture with stirring to about 80° C until the resin is dissolved.

A turbid solution is obtained which can be readily diluted with water.

Solids content: 20%, pH: 7.7.

EXAMPLE 4

A mixture of 18.2 g (0.1 mole of maleic anhydride equivalent) of maleic anhydride/diketene copolymer (1:1), 9.3 g (0.05 mole) of lauryl alcohol, 37.5 g (0.05 mole) of methoxypolyethylene glycol 750, 6.5 g (0.088 mole) of n-butanol and 0.2 g of p-toluenesulphonic acid is refluxed for 24 hours in 360 g of dioxan. The dioxan is then removed by vacuum distillation.

Yield: 71 g (68.5 g of dry substance) of a wax-like product.

Acid number: 129; viscosity number ($\eta$): 0.074.

The sodium salt is manfactured by adding 21 g of 30% sodium hydroxide solution and 250 g of water thereto and heating the mixture with stirring to about 80° C until the resin is dissolved.

A turbid solution is obtained which can be readily diluted with water.

Solids content: 20%, pH: 7.3.

EXAMPLE 5

A mixture of 18.2 g (0.1 mole of maleic anhydride equivalent) of maleic anhydride/diketene copolymer (1:1), 13.5 g (0.05 mole) of stearyl alcohol, 37.5 g (0.05 mole) of methoxypolyethylene glycol 750 and 0.2 g of p-toluenesulphonic acid is refluxed for 24 hours in 360 g of dioxan. The dioxan is then removed by vacuum distillation. Yield: 72 g (68.5 g of dry substance) of a wax-like product.

Acid number: 136; viscosity number ($\eta$): 0.113.

The sodium salt is manufactured by adding to this product 19.5 g of 30% sodium hydroxide solution and 365.5 g of water and heating the mixture with stirring to about 80° C until the resin is dissolved.

An opalascent solution is obtained which is readily miscible with water.

Solids content: 15%, pH: 6.2.

EXAMPLE 6

A mixture of 18.2 g (0.1 mole of maleic anhydride equivalent) of maleic anhydride/diketene copolymer (1:1), 16.3 g (0.06 mole) of stearyl alcohol, 30 g (0.04 mole) of methoxypolyethylene glycol 750 and 0.2 g of p-toluenesulphonic acid is refluxed for 24 hours in 400 g of dioxan. The dioxan is then removed by vacuum distillation. Yield: 70 g (64 g of dry substance) of a wax-like product.

Acid number: 152; viscosity number ($\eta$): 0.205.

The sodium salt is manfactured by adding to this product 23 g of 30% sodium hydroxide solution and 333 g of water and heating the mixture with stirring to about 80° until the resin is dissolved.

A turbid solution is obtained which can be readily diluted with water.

Solids content: 15%, pH: 8.5.

EXAMPLE 7

A mixture of 18.2 g (0.1 mole of maleic anhydride equivalent) of maleic anhydride/diketene copolymer (1:1), 13.5 g (0.05 mole) of stearyl alcohol, 21.5 g (0.05 mole) of methoxypolyethylene glycol 430 and 0.2 g of p-toluenesulphonic acid is refluxed for 24 hours in 360 g of dioxan. The dioxan is then removed by vacuum distillation. Yield: 56 g (53 g of dry substance) of a wax-like product.

Acid number: 153; viscosity number ($\eta$):0.115.

The sodium salt is manufactured by adding to this product 26 g of 30% sodium hydroxide solution and 272 g of deionised water and heating the mixture with stirring to about 80° C until the resin is dissolved.

A turbid solution is obtained which can be readily diluted with water.

Solids content: 15%, pH value: 10.

EXAMPLE 8

A mixture of 18.36 g (0.1 mole of maleic anhydride equivalent) of maleic anhydride/diketene/n-butyl vinyl ether copolymer (1:0.9:0.1), 6.75 g (0.025 mole) of stearyl alcohol, 37.5 g (0.05 mole) of methoxypolyethylene glycol 750, 1.85 g (0.025 mole) of n-butanol and 0.5 g of p-toluenesulphonic acid is refluxed for 24 hours in 360 g of dioxan. The dioxan is then removed by vacuum distillation. Yield: 72 g of residue (64 g of solid matter).

Acid number: 146; viscosity number ($\eta$): 0.09.

The sodium salt is manufactured by adding 20 g of 30% of sodium hydroxide solution and 228 g of deionised water and heating the mixture with stirring to about 80° C until the resin is dissolved.

Solids content: 20%, pH value: 6.8.

EXAMPLE 9

A mixture of 18.2 g (0.1 mole of maleic anhydride equivalent) of maleic anhydride/diketene copolymer (1:1), 75 g (0.1 mole) of methoxypolyethylene glycol 750 and 0.5 g of p-toluenesulphonic acid is refluxed for 24 hours in 360 g of dioxan. The dioxan is then removed by vacuum distillation. Yield: 95 g (93 g of dry substance) of a viscose resin.

Acid number: 104; viscosity number ($\eta$): 0.054.

The sodium salt is manufactured by adding to this product 23.5 g of 30% sodium hydroxide solution and 346.5 g of water and heating the mixture with stirring at about 80° C until the resin is dissolved. A clear solution is obtained.

Solids content: 20%, pH vlaue: 8.4.

EXAMPLE 10

A mixture of 36.4 g (0.2 mole of maleic anhydride equivalent) of maleic anhydride/diketene copolymer (1:1), 7.4 g (0.1 mole) of n-butanol, 75 g (0.1 mole) of methoxypolyethylene glycol 750 and 0.2 g of p-toluenesulphonic acid is refluxed together with 360 g of dioxan for 24 hours. The dioxan is then removed by vacuum distillation. Yield: 124 g (118 g of dry substance) of a wax-like product.

Acid number: 154; viscosity number ($\eta$): 0.083.

The sodium salt is manufactured by adding 43 g of 30% sodium hydroxide solution and 423 g of deionised water thereto and heating the mixture with stirring to about 80° C until the resin is dissolved.

An opalescent solution which can be readily diluted with water is obtained.

Solids content: 20%, pH value: 7.1.

EXAMPLE 11

A mixture of 36.4 g (0.2 maleic anhydride equivalent) of maleic anhydride/diketene copolymer (1:1), 1.6 g (0.05 mole) of methanol, 13.5 g (0.05 mole) of stearyl alcohol, 75 g (0.1 mole) of methoxypolyethylene glycol 750 and 0.2 g of p-toluenesulphonic acid is refluxed in 350 g of dioxan for 24 hours.

Yield: 152 g (125 g of solid matter) of a wax-like product.

Acid number: 157.4; viscosity number ($\eta$): 0.098.

The sodium salt is manufactured by adding 35.4 g of 30% sodium hydroxide solution and 367 g of deionised water to 129 g (106 g of solid matter) of the above product and heating the mixture with stirring to about 80° C until the resin is dissolved.

A turbid solution which can be readily diluted with water is obtained.

Solids content: 20%, pH: 7.1.

EXAMPLE 12

A mixture of 18.42 g (0.1 maleic anhydride equivalent) of maleic anhydride/diketene/chloroethyl vinyl ether copolymer (1:0.9:0.1), 6.75 g (0.025 mole) of stearyl alcohol, 37.5 g (0.05 mole) of methoxypolyethylene glycol 750 and 0.2 g of p-toluenesulphonic acid is refluxed in 360 g of dioxan for 24 hours. The dioxan is then removed by vacuum distillation. Yield: 69 g (62 g of solid matter) of a wax-like product.

Acid number: 164; viscosity number ($\eta$): 0.081.

The sodium salt is manufactured by adding 12.2 g of 30% sodium hydroxide solution and 197 g of deionised water to the above product and heating the mixture with stirring to about 80° C until the resin is dissolved.

A turbid solution which can be readily diluted with water is obtained.

Solids content: 20%, pH: 6.1

EXAMPLE 13

A mixture of 18.94 g (0.1 maleic anhydride equivalent) of maleic anhydride/diketene/2-ethylhexyl vinyl ethyl copolymer (1:0.9:0.1), 6.75 g (0.025 mole) of stearyl alcohol, 37.5 g (0.05 mole) of methoxypolyethylene glycol 750 and 0.2 g of p-toluenesulphonic acid is refluxed in 360 g of dioxan for 24 hours. The dioxan is then removed by vacuum distillation.

Yield: 70.6 g (62 g of solid matter) of a wax-like product.

Acid number: 143.8; viscosity number ($\eta$): 0.061.

The sodium salt is manufactured by adding 13 g of 30% sodium hydroxide solution and 193 g deionised water to the above product and heating the mixture with stirring to about 80° C until the resin is dissolved. A turbid solution which can be readily diluted with water is obtained.

Solids content: 20%, pH: 6.4.

EXAMPLE 14

A mixture of 18.52 g (0.1 maleic anhydride equivalent) of maleic anhydride/diketene/n-butyl vinyl ether copolymer (1:0.8:0.2), 6.75 g (0.025 mole) of stearyl alcohol and 0.2 g of p-toluenesulphonic acid is refluxed in 360 g of dioxan for 24 hours. The dioxan is then removed by vacuum distillation.

Yield: 70.5 g (62 g of solid matter) of a wax-like product.

Acid number: 158.6; viscosity number ($\eta$): 0.114.

The sodium salt is manufactured by adding 12 g of 30% sodium hydroxide solution and 191 g of deionised water and heating the mixture to about 80° C until the resin is dissolved. A turbid solution which can be readily diluted with water is obtained.

Solids content: 20%, pH: 6.7.

EXAMPLE 15

A mixture of 20.32 g (0.1 maleic anhydride equivalent) of maleic anhydride/diketene/stearyl vinyl ether copolymer (1:0.9:0.1), 6.75 g (0.025 mole) of stearyl alcohol, 37.5 g (0.5 mole) of methoxypolyethylene glycol 750 and 0.2 g of p-toluenesulphonic is refluxed in 360 g of dioxan for 24 hours. The dioxan is then removed by vacuum distillation. Yield: 72.8g (64 g of solid matter) of a wax-like product.

Acid number: 149; viscosity number: ($\eta$): 0.083.

The sodium salt is manufactured by adding 13.2 g of a 30% sodium hydroxide solution and 204.8 g of deionised water to the above product and heating the mixture to about 80° C until the resin is dissolved.

A turbid solution which can be readily diluted with water is obtained.

Solids content: 20%, pH: 7.0.

EXAMPLE 16

A mixture of 18.36 g (0.1 maleic anhydride equivalent) of maleic anhydride/diketene/isobutyl vinyl ether copolymer (1:0.9:0.1), 6.75 g (0.025 mole) of stearyl alcohol, 37.5 g (0.05 mole) of methoxypolyethylene glycol 750 and 0.2 g of p-toluenesulphonic acid is refluxed in 360 g of dioxan for 24 hours. The dioxan is then removed by vacuum distillation.

Yield: 68.3 g (62 g of solid matter) of a wax-like product.

Acid number: 159; viscosity number ($\eta$): 0.059.

The sodium salt is manufactured by adding 13 g of 30% sodium hydroxide solution and 199 g of deionised water to the above product and heating the mixture to about 80° C until the resin is dissolved. A turbid solution which can be readily diluted with water is obtained.

Solids content: 20%, pH: 6.6.

EXAMPLE 17

A mixture of 18.68 g (0.1 maleic anhydride equivalent) of maleic anhydride/diketene/n-butyl vinyl ether copolymer (1:0.7:0.3), 6.75 g (0.025 mole) of stearyl alcohol, 37.5 g (0.05 mole) of methoxypolyethylene glycol 750 and 0.2 g of p-toluenesulphonic acid is refluxed in 360 g of dioxan for 24 hours. The dioxan is then removed by vacuum distillation.

Yield: 69 g (62 g of solid matter) of wax-like product.

Acid number: 143.7; viscosity number ($\eta$): 0.10.

The sodium salt is manufactured by adding 13 g of 30% sodium hydroxide solution and 199 g of deionised water to the above product and heating the mixture to about 80° C until the resin is dissolved. A turbid solution which can be readily diluted with water is obtained.

Solids content: 20%, pH: 6.7.

EXAMPLE 18

A mixture of 291 g (1.6 of maleic anhydride equivalent) of maleic anhydride/diketene copolymer (1:1), 600 g (0.8 mole) of methoxypolyethylene glycol 750 and 6 g p-toluenesulphonic acid is refluxed in 3088 g of dioxan for 14½ hours. Then 108 g (0.4 mole) of stearyl alcohol are added and the mixture is refluxed for a further 9 hours. The dioxan is then removed by vacuum distillation.

Yield: 1150 g (999 g of solid matter) of a wax-like product.

Acid number: 163.6; viscosity number ($\eta$): 0.084.

The sodium salt is manufactured by adding 17.9 g of 30% sodium hydroxide solution and 1632 g of deionised water to the above product and heating the mixture to about 80° C until the resin is dissolved. A turbid solution which can be readily diluted with water is obtained.

Solids content: 20%, pH: 3.4.

EXAMPLE 19

A tufted polyamide carpet is padded with the polymer solution according to Example 3 and squeezed out to about 100% pick-up. The carpet is then dried for 10 minutes at 150° C.

The electrostatic behaviour as well as colour change and antisoiling are determined.

|  | finished | non-finished |
|---|---|---|
| Resistance[Ω] | $5.10^{10}$–$2.10^{11}$ | $>10^{13}$ |
| Maximum charge [V] | 200–600 | ~10000 |
| Antisoiling | as untreated material | — |
| Handle |  | — |
| Colour changes | none |  |

The electrostatic behaviour of the finished carpet material is very good. The other properties tested, especially the antisoiling and the handle, are not adversely affected by the finish.

EXAMPLE 20

A coloured fabric of polyamide[poly(hexamethylene adipic acid amide)] is padded with the polymer solution according to Example 3 and squeezed out to about 100% pick-up. The fabric is then dried for 10 minutes at 150°. The electrostatic behaviour of the finished fabric is very good. The antisoiling behaviour and the handle are not adversely affected and colour changes do not occur. The fastness to rubbing (dry and wet) and the water fastness (resistance to the prolonged action of water) were further tested. The ratings 1 to 5 are used in both tests, 5 being the best rating.

| Fastness to rubbing: | treated: | 4–5 (dry); | 4–5 (wet) |
|---|---|---|---|
|  | untreated: | 5 (dry); | 5 (wet) |
| water fastness: |  |  | rating |
| treated | polyamide fabric |  | 3–4 |
|  | polyamide fabric | ⎫ accompanying | 5 |
|  | cotton fabric | ⎭ material | 5 |
| untreated | polyamide fabric |  | 4–5 |
|  | polyamide fabric | ⎫ accompanying | 5 |
|  | cotton fabric | ⎭ material | 5 |

Comparably good effects are also obtained using the polymer solutions of Examples 2 and 4 to 10.

Water fastness test: A sample of the treated fabric (polyamide) is laid in water between two undyed fabrics (polyamide and cotton). The three pieces of material are allowed to drain and then subjected to a given stress. The samples and the accompanying fabrics are dried separately. The colour change of the sample and the soiling are evaluated (no change in colour of the sample and no soiling of the accompanying material is given a rating of 5).

EXAMPLE 21

A coloured polyamide carpet (500 g/m², tufted) is padded with polymer solutions (1% solids content) of the Examples listed in Table 1 and squeezed out to 100% pick-up.

The carpet is then dried for 10 minutes at 150° C. The electrostatic (resistance, charge after 60 steps) and the antisoiling behaviour, the handle and the colour change as well as the fastness to dry and wet rubbing are determined.

TABLE I

| Copolymer | Resistance [Ω] | Charge [V] | Rubbing Soiling | Handle | Colour change | fastness to dry | wet |
|---|---|---|---|---|---|---|---|
| Ex. 11 | 4.4·10¹⁰ | 160–870 | a | b | none | 3–4 | 4 |
| Ex. 12 | 4.4·10¹⁰ | 50–800 | a | b | none | 4–5 | 4–5 |
| Ex. 13 | 4.4·10¹⁰ | 70–875 | b | c | none | 4–5 | 4–5 |
| Ex. 14 | 4.4·10¹⁰ | 90–770 | b | c | none | 4 | 4 |
| Ex. 15 | 2.6·10¹⁰ | 95–870 | b | c | none | 4 | –4 |
| Ex. 16 | 4.4·10¹⁰ | 80–500 | b | b | none | 4 | 4 |
| Ex. 17 | 4.4·10¹⁰ | 200–1215 | a | c | none | 4–5 | 4–5 |
| Ex. 18 | 2.6·10¹⁰ | 9–125 | b | b | none | 4–5 | 4–5 |
| untreated | 10¹³ | 9620–18000 | — | — | — | 5 | 5 | a = less than untreated
b = as untreated
c = softer than untreated

The rating from 1 to 5 is used in determining the fastness to rubbing, 5 being the highest rating.

The electrostatic behaviour of the finished carpet material is very good.

The other properties of the material are not adversely affected by the antistatic finish.

EXAMPLE 22

Human hair is treated with a mixture of 20 parts of the neutralised polymer of Example 3 (10% aqueous solution) and 80 parts of water, and subsequently dried.

The treated hair as well set and does not stick together. It is easy to brush and comb, has a natural gloss, is easily rinsed out, and has not electrostatic charge.

We claim:

1. Carboxy and ester groups containing addition copolymers with on average, a total of 3 to 900 recurring units and consisting of units of the formula

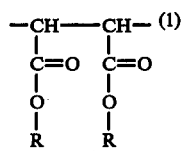  (1)    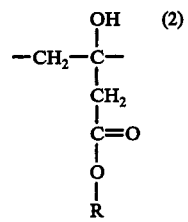  (2)

and optionally

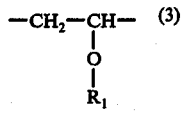  (3)

wherein
R is hydrogen, an alkali metal, an alkaline earth metal, amine, ammonium or the radical of an alcohol component which is a mixture of an alcohol of 1 to 18 carbon atoms and an ethylene- or polyethylene glycol monoalkyl ether of the formula

where
$R_2$ is alkyl of 1 to 6 carbon atoms, and
m is an integer of 1 to 80;
$R_1$ is substituted or unsubstituted alkyl of 1 to 22 carbon atoms, the ratio of carboxy to ester groups is 5:1 to 1:5 and the ratio of the recurring units (1), (2) and (3) is 1:(0.7 to 0.9); (0.3 to 0.1), and the ratio of the recurring units of (1) and (2) in the absence of (3) is 1:1; and said addition polymers having an average molecular weight by vapor pressure osmosis of 800 to 45,000.

2. Copolymers according to claim 1, wherein the ratio of carboxy groups to ester groups is 2:1 to 1:2.

3. Copolymers according to claim 1, wherein the ratio of carboxy groups to ester groups is 5:1 to 1:2.

4. Copolymers according to claim 1 which contain on average in each molecule together 3 to 900 recurring units of the formulae

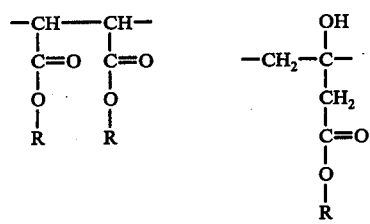

wherein
R has the meaning as indicated in claim 1 and the ratio of the recurring units is 1:1.

5. Copolymers according to claim 1 which contain on average in each molecule together 3 to 300 units.

6. Copolymers according to claim 1 which contain on average in each molecule together 6 to 150 units.

7. Copolymers according to claim 1 with no average molecular weight of 1,000 to 20,000.

8. Copolymers according to claim 1 wherein the vinyl alkyl ethers contain 1 to 22 carbon atoms in the alkyl moiety.

9. Copolymers according to claim 1 wherein the vinyl alkyl ethers contain 2 to 18 carbon atoms in the alkyl moiety.

10. Copolymers according to claim 1 wherein the vinyl alkyl ethers contain 2 to 8 carbon atoms in the alkyl moiety.

11. Copolymers according to claim 1 wherein the alcohol component is a mixture of polyethylene glycol monoalkyl ethers and an alcohol of 1 to 8 carbon atoms.

12. Copolymers according to claim 1 wherein the alcohol component is a mixture of polyethylene glycol monoalkyl ethers and an alcohol of 1 to 4 carbon atoms.

13. Copolymers according to claim 1 wherein the alcohol component is a mixture of polyethylene glycol monoalkyl ethers and an alcohol of 9 to 18 carbon atoms.

14. Copolymers according to claim 1 wherein the alcohol component is a mixture of polyethylene glycol monoalkyl ethers and an alcohol of 12 to 18 carbon atoms.

15. Copolymers according to claim 1 wherein the alcohol component is a mixture of polyethylene glycol monoalkyl ethers, an alcohol of 1 to 8 carbon atoms and an alcohol of 9 to 18 carbon atoms.

16. Copolymers according to claim 1 wherein the carboxy groups are in the form of alkali metal, alkaline earth metal, amine or ammonium salts.

* * * * *